Figure 1:
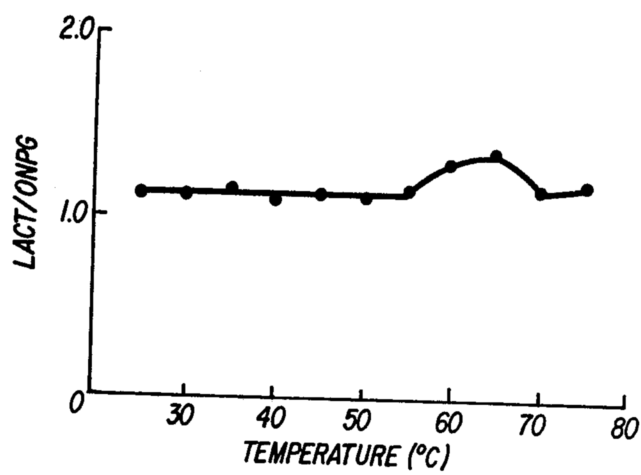

United States Patent [19]

Iida et al.

[11] 4,237,230

[45] Dec. 2, 1980

[54] NOVEL LACTASE

[75] Inventors: Takao Iida; Sho Ozaki, both of Shiga; Toshihiko Kotaka, Otsu, all of Japan

[73] Assignee: Daiwa Kasei Kabushiki Kaisha, Osaka, Japan

[21] Appl. No.: 52,444

[22] Filed: Jun. 26, 1979

Related U.S. Application Data

[63] Continuation-in-part of Ser. No. 884,421, Mar. 8, 1978, abandoned.

[30] Foreign Application Priority Data

May 31, 1977 [JP] Japan .................................. 52-64347

[51] Int. Cl.[3] .............................................. C12N 9/38

[52] U.S. Cl. ..................................... 435/207; 435/835

[58] Field of Search .......................................... 435/207

[56] References Cited

U.S. PATENT DOCUMENTS

| | | | |
|---|---|---|---|
| 3,816,259 | 6/1974 | Collinge et al. | 435/207 |
| 4,179,335 | 12/1979 | Long et al. | 435/207 |

FOREIGN PATENT DOCUMENTS 2554407 10/1976 Fed. Rep. of Germany .

*Primary Examiner*—Lionel M. Shapiro

*Attorney, Agent, or Firm*—Stevens, Davis, Miller & Mosher

[57] ABSTRACT

A novel lactase having a molecular weight of about $3\times 10^5$, an optimum pH value of about 6.0, an optimum temperature of about 60° C. and at least 1 of the ratio of the activity for hydrolyzing lactose to the activity for hydrolyzing a synthetic substrate: o-nitrophenyl-β-D-galactopyranoside (Lact/ONPG ratio), which is produced by cultivating a microorganism of the genus Bacillus being capable of producing the enzyme, particularly *Bacillus circulans* LOB 377 (ATCC No. 31382) and isolating from the culture broth. This novel lactase is characteristic in the excellent thermostability and the high Lact/ONPG ratio and hence is useful for treating milk and milk products as well as for preventing diarrhea due to lactose intolerance, especially in babies and infants.

4 Claims, 10 Drawing Figures

NOVEL LACTASE

This is a continuation-in-part application of U.S. Ser. No. 884,421 filed on Mar. 8, 1978, now abandoned.

The present invention relates to a novel lactase having an excellent thermostability and a method for the production thereof. More particularly, it relates to a novel lactase having an excellent thermostability and high activity for hydrolyzing lactose, which is produced by cultivating a microorganism of the genus Bacillus being capable of producing the novel lactase.

Lactase is an enzyme which is also called as β-galactosidase and can hydrolyze β-galactoside bond contained in lactose or the like to release D-galactose. It is known that this enzyme is distributed various microorganisms such as bacteria and fungi, and also in various plants and animals. However, it has practically been used only for a restricted purpose. That is, only lactase produced by fungi has been used for preventing diarrhea due to lactose intolerance, especially in babies and infants. Various lactases have hitherto been studied with aiming at the development of the utility thereof as a treating agent for milk and milk products, but they have never been practically used for such purpose because of the following problems:

(1) The most of the known lactases do not show a really high activity for hydrolyzing lactose. The activity of lactase is usually shown by the activity for hydrolyzing a synthetic substrate: o-nitrophenyl-β-D-galactopyranoside (hereinafter, referred to as "ONPG"), because it can easily be measured. However, the hydrolyzing activity against the synthetic substrate does not necessarily coincide with the activity against the real substrate: lactose, and known lactases have a ratio of the lactose-hydrolyzing activity to the ONPG-hydrolyzing activity (hereinafter, referred to as "Lact/ONPG ratio") of far smaller than 1.

(2) For the purpose of treating milk and milk products, the lactase should have an optimum pH value around neutral and a higher optimum temperature in view of raising the reaction rate and of preventing putrefaction of the milk and milk products, but most known lactases do not satisfy both conditions.

(3) It should be avoided to coagulate casein contained in the milk, and hence, it is preferable that the lactase is contaminated with protease as little as possible. Besides, it is preferable that the lactase can be produced in the culture broth without extracting from the cells of microorganisms.

As the result of screening many kinds of soil microorganisms for the purpose of finding a novel lactase eliminating the above defects in the known lactases, it has now been found that a microorganism of the genus Bacillus can produce the desired novel lactase.

An object of the present invention is to provide a novel lactase having an excellent thermostability and a high Lact/ONPG ratio.

Another object of the invention is to provide a method for producing the novel lactase by cultivating a microorganism of the genus Bacillus being capable of producing the novel lactase, particularly, a newly isolated strain of *Bacillus circulans.*

These and other objects of the invention will be apparent from the following disclosure.

The novel lactase of the present invention is characteristic in that it has an activity for hydrolyzing lactose equal to or more than the activity for hydrolyzing the synthetic substrate: ONPG, i.e. 1 or more of the Lact/ONPG ratio, an optimum pH value of about 6.0 and an optimum temperature of about 60° C. Moreover, according to the method of the present invention, the lactase can be produced in the cultivation broth with little or a little by-production of protease, and hence, it can be used for the treatment of milk and milk products without undesirable coagulation of casein.

The characteristics of the present lactase are compared with those of the known lactases in the following Table 1.

Table 1

| Characteristics | Lactase of the present invention | Lactase of reference*1 | | | |
|---|---|---|---|---|---|
| | | A | B | C | D |
| Lact/ONPG ratio | 1–2 | $\frac{1}{4}$ | $\frac{1}{4}$ | $\frac{1}{3}$ | 1/28 |
| Optimum temp. (°C.) | 60 | 50 | 50 | 60–70 | 40 |
| Optimum pH value | 6.0 | 4.5 | 4.5 | 4.0 | 7.0 |
| Stable pH range | 4.5–10.0 | 4.5–9.0 | 4.5–7.0 | 2.0–8.0 | 6.5–8.0 |
| Protease | –*2 | – | + | – | Unknown |
| Manner of production*3 | Secretion | Secretion | Secretion | Secretion | In the cells |

[Remarks]:

*1The lactases of reference are produced by the following microorganisms:
A *Aspergillus oryzae* (Lactase sold by Tokyo Tanabe Pharmaceutical Co., Ltd.)
B *Penicillium citrinum* (cf. Yasuto Watanabe, "Research of Production of Lactase and Application thereof to Milk Products", the text in the lecture for popularizing the effect of the subsidy project for technical research and development in the fiscal year of 1974, sponsered by Small and Medium Enterprises Agency and Osaka City, Japan, November, 1975)
C *Aspergillus niger* (Lactase sold by Miles Laboratories Incorporated)
D *Escherichia coli* (cf. Arakawa et al, Biochemistry, Vol. 46, page 796, 1974)
*2Under certain condition protease is little produced, but under some conditions protease is occasionally produced in a small amount.
*3By the cultivation of a microorganism, lactase is produced in the culture broth or in the cells of the microorganism. Secretion means that the lactase is produced in the culture broth.

As is clear from Table 1, the lactase of the present invention has characteristics different from those of the known lactases.

Besides, it is disclosed in German Offenlegungsschrift 25 54 407 that a thermostable lactase can be produced by cultivating *Bacillus coagulans,* wherein the lactase is produced in the cells of the microorganism. While the activities of this lactase are not disclosed, it will be expected that this lactase will not show such a high Lact/ONPG ratio as that of the present lactase. The lactase of the present invention will be clearly different from that of the German patent application in the high Lact/ONPG ratio and the manner of production.

According to the present invention, the desired lactase can be produced by cultivating a strain of the genus Bacillus which was newly isolated from a soil. This strain has the following characteristics.

Vegetative rods: 0.6μ to 0.8μ by 3.8μ to 5.0μ; motile; gram-negative
Spores: 1.0μ by 1.5μ; oval
Sporangia: definitely bulged
Nutrient agar slants: growth abundant; yellowish brown; smooth
Catalase reaction: positive
Growth in anaerobic agar: positive
Voges-Proskauer test: negative
pH in Voges-Proskauer broth: lower than 6.0
Maximum temperature of growth: 45° C.
Growth at pH 5.7: negative
Nutrient broth: growth abundant
NaCl broth: no growth in broth containing 5% NaCl Acid and gas from carbohydrates: acid produced without gas from glucose and lactose; acid not produced without gas from arabinose, mannitol and xylose
Hydrolysis of starch: positive
Utilization of citrate and propionate: positive about citrate, negative about propionate
Reduction of nitrate to nitrite: positive
Crystalline dextrin: negative
Production of dihydroxyacetone: negative
Production of indole: negative
Deamination of phenylalanine: negative
Decomposition of casein: slightly decomposed
Hydrolysis of gelatin: negative
Decomposition of tyrosine: not definitely positive
Reaction in litmus milk: neutral On the basis of these taxonomical characteristics, this strain can be regarded as *Bacillus megaterium, stearothermophilus* or circulans according to "The Genus Bacillus," Agriculture Handbook 427, U.S. Dept. of Agriculture (1973), but *Bacillus megaterium* is evidently different from this strain in cell size and *Bacillus stearothermophilus* also is different in growth temperature. It, therefore, may be concluded that strain LOB 377 belongs to *Bacillus circulans* despite slight differences from the type species, and then this strain has been designated as *Bacillus circulans* LOB 377. This strain is deposited with American Type Culture Collection, U.S.A. as ATCC No. 31382 and BIKOKEN (Fermentation Research Institute, Agency of Industrial Science and Technology), Japan as FERM-P No. 4068.

In the present invention the microorganism of the genus Bacillus being capable of producing the novel lactase includes the above wild type strain: *Bacillus circulans* LOB 377 and also any natural or artificial mutant thereof unless the ability of producing the novel lactase is lost.

According to the present invention, the novel lactase can be produced by cultivating a microorganism of the genus Bacillus being capable of producing the novel lactase, especially a wild type strain: *Bacillus circulans* LOB 377, in a conventional liquid or solid culture medium containing carbon sources, nitrogen sources, minerals, vitamins, or the like, and thereby, the desired lactase is accumulated in the culture broth.

Carbon sources used in the present medium include glucose, sucrose, lactose, maltose, dextrin, or the like. Nitrogen sources include corn steep liquor, soy bean powder, peptone, meat extract, yeast extract, amino acids, ammonium salts, nitrates, or the like. Minerals include phosphates, magnesium, calcium, potassium, sodium, or the like.

The culture is not limited to a particular methods, but can be carried out under an aerobic condition by a conventional culture method, such as shake culture or submerged culture with aeration and agitation. Temperature of the culture may be variable within a certain range, at which the microorganism can grow and produce the desired lactase, but is preferably in the range of 30° to 40° C. Period of the culture may be variable depending on other culture conditions, but is usually in the range of from 12 hours to 5 days. Practically, the best period of the culture may be determined by measuring the time when the yield of the desired lactase reaches at maximum.

After the cultivation, the desired lactase is isolated. In the present invention, the lactase is secreted outside of the cells of the microorganism, and hence, the obtained culture broth containing the desired lactase can be submitted to isolation, recovery and purification by means of conventional methods. For instance, the cells of the microorganism are removed off from the culture broth by filtration or extraction with water or a suitable organic solvent and then the desired lactase is separated from the culture broth by salting-out with a soluble salt (e.g. ammonium sulfate) and then dried to give a crude enzyme powder. The crude enzyme powder is purified in a conventional manner, for instance, by a dialysis using a 0.01 M Tris-HCl buffer (pH 8.3) followed by adsorption onto DEAE Sephadex A-50 and elution therefrom. The thus purified enzyme is dried under reduced pressure or lyophilized to give a solid enzyme product.

The novel lactase of the present invention has the following characteristics.

(1) Activity:

It acts specifically on $\beta$-D-galactopyranosyl derivative to release D-galactose.

Figure 2:
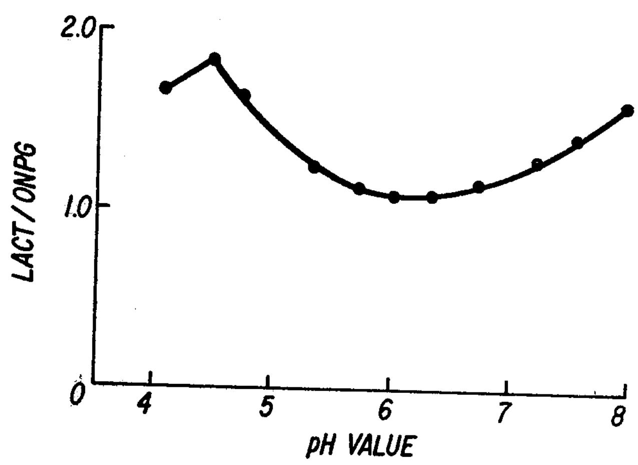

(2) Substrate specificity:

Generally, known lactases have a far lower activity for hydrolyzing natural substrate: lactose than the activity for hydrolyzing a synthetic substrate: ONPG, but the novel lactase of the present invention has a high activity for hydrolyzing lactose and has a Lact/ONPG ratio of 1 to 2. The substrate specificity of the present lactase varies depending on the temperature and pH value. Change of the substrate specificity of the present lactase depending on the temperature is shown in the accompanying FIG. 1 and that depending on the pH value is shown in FIG. 2, respectively.

(3) Measurement of the activity value (unit)

(a) Measurement of the activity for hydrolyzing lactose

To a 0.1 M acetate buffer solution (pH 6.0, 4 ml) containing 5% by weight of lactose is added the present lactase (1 ml). The mixture is reacted at 40° C. for 15 minutes. The reaction mixture (1 ml) is added to a 10% aqueous sodium carbonate solution (1 ml) to stop the reaction. By measuring the amount of the produced glucose, the amount of the hydrolyzed lactose is calculated. The amount of the enzyme required for hydrolyzing 1 $\mu$M of lactose per one minute is defined as "1 Lact unit".

(b) Measurement of the activity for hydrolyzing ONPG

To a 0.1 M acetate buffer solution (pH 6.0, 4 ml) containing 0.25% by weight of ONPG is added the present lactase (1 ml). The mixture is reacted at 40° C. for 15 minutes. The reaction mixture (1 ml) is added to a 10% aqueous sodium carbonate solution (1 ml) to stop the reaction. By measuring the amount of the produced o-nitrophenol, the amount of the hydrolyzed ONPG is calculated. The amount of the enzyme required for hydrolyzing 1 $\mu$M of ONPG per one minute is defined as "1 ONPG unit."

(4) Optimum pH value and stable pH range

Figure 3:
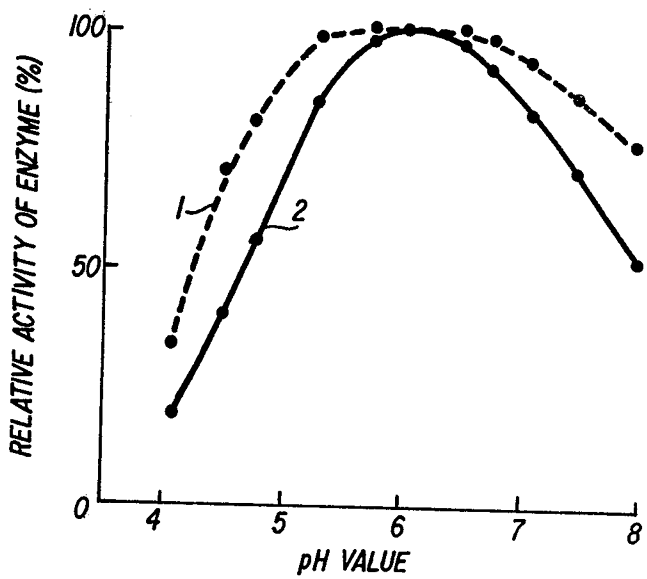
Figure 4:
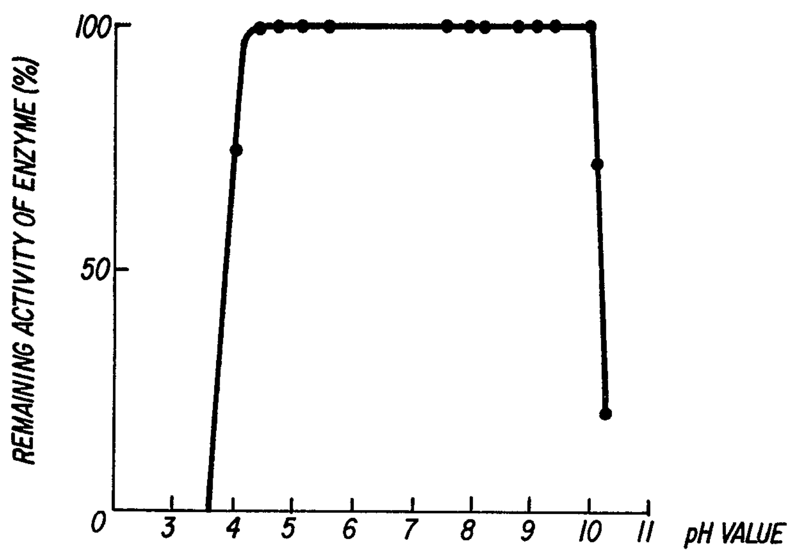

The optimum pH value and stable pH range of the present lactase are shown in the accompanying FIG. 3 and FIG. 4, respectively. FIG. 3 shows the relative activity (%) of the enzyme with the change of pH value when the enzyme is reacted in the same manner as disclosed in the above item (3) except that McIlvaine's buffer solution (citric acid-disodium hydrogen phosphate buffer) is used instead of the acetate buffer solution, wherein the curve 1 is the data in case of lactose substrate and the curve 2 is the data in case of ONPG substrate. As is clear from FIG. 3, the optimum pH value of the present lactase is at around 6.0 and the case of lactose substrate (the curve 1) has a wider range of the optimum pH value than the case of ONPG substrate (the curve 2). FIG. 4 shows the remaining activity (%) of the enzyme at each pH value when the enzyme is kept in McIlvaine's buffer solution or glycine-sodium hydroxide buffer solution at 30° C. for 1 hour at the respective pH value. As is clear from FIG. 4, the stable pH range of the present lactase is in the range of 4.5 to 10.0.

(5) Optimum temperature and stable temperature range

Figure 5:
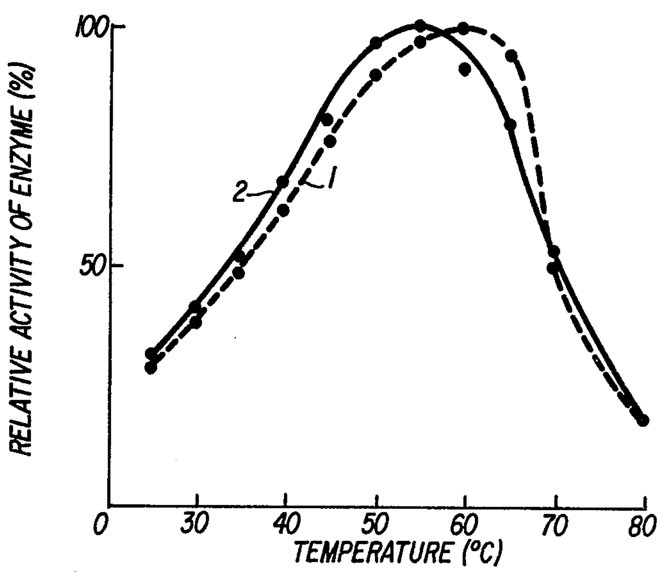
Figure 6:
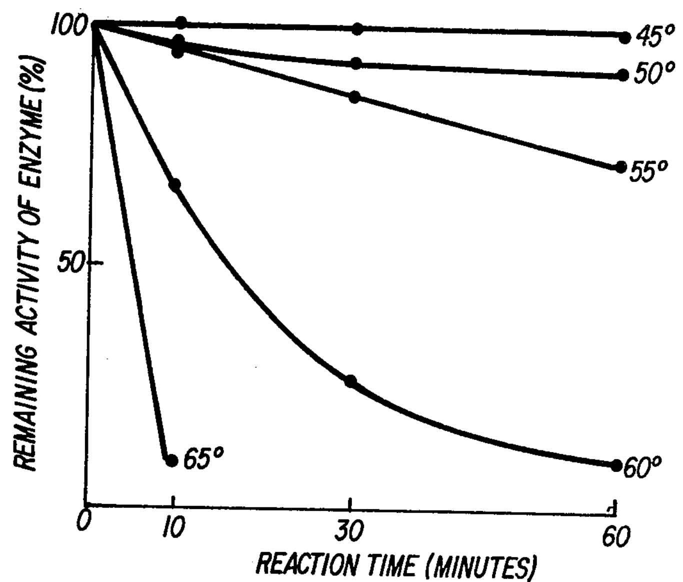

The optimum temperature and stable temperature range of the present lactase are shown in the accompanying FIG. 5 and FIG. 6, respectively. FIG. 5 shows the change of the relative activity (%) of the enzyme when the enzyme is reacted at pH 6.0 and at the designated temperature for 15 minutes in the same manner as disclosed in the above item (3), wherein the curve 1 is the data in case of lactose substrate and the curve 2 is the data in case of ONPG substrate. As is clear from FIG. 5, the optimum temperature of the present lactase is about 55° C. in case of ONPG substrate (the curve 2) and about 60° C. in case of lactose substrate (the curve 1). FIG. 6 shows the remaining activity (%) of the enzyme when the enzyme is kept at pH 6.0 and at the designated temperature for 10, 30 or 60 minutes. As is clear from FIG. 6, the present lactase has a remaining activity of not less than 90% in case of keeping at 50° C. for 1 hour and about 70% in case of keeping at 55° C. for 1 hour.

(6) Inhibition and activation

The activity of the present lactase is inhibited by ferric chloride (10 mM), zinc chloride (10 mM) and glucose (20 mM) and is activated by galactose (20 mM).

(7) Purification

The culture broth is filtered to remove the cells. To the filtrate is added ammonium sulfate (53% saturation). The mixture is agitated and the produced crude enzyme is collected by filtration. The crude enzyme is subjected to dialysis using a Tris buffer solution (pH 8.3) and is adsorbed onto a column filled with DEAE Sephadex A-25 and then eluted with a 0.35 M aqueous potassium chloride solution. The eluted fraction having ONPG-hydrolyzing activity is further adsorbed onto DEAE Sephadex A-50 and then eluted to give the desired purified enzyme.

(8) Molecular weight

The lactase has a molecular weight of about $3\times10^5$ (measured by gel filtration using Sephadex G 200).

The novel lactase of the present invention is useful not only as a medicine for preventing diarrhea due to lactose intolerance, especially in babies and infants, but also for treating milk and milk products, for example, concentrated milk, ice cream, cheese, cultured milk and whey. This lactase is usually used under the conditions of a pH value of 4.5 to 10 and a temperature of 40° to 60° C., but if necessary, it may be used at a lower temperature, for instance, at about 5° C., at which milk is usually stored.

The present invention is illustrated by the following Examples but is not limited thereto. In Examples "%" means % by weight unless specified otherwise.

EXAMPLE 1

A liquid medium (pH 7.0, each 100 ml) containing meat extract (0.5%), polypeptone (1%), sodium chloride (0.2%) and lactose (0.1%) is added to flasks, which is sterilized at 120° C. for 15 minutes in an autoclave. The isolated LOB 377 strain (one platinum loop) is inoculated onto the medium and is cultivated at 38° C. for one day with shaking by a shaking machine. The culture broth thus obtained has an activity of 0.3 ONPG unit/ml and 0.3 Lact unit/ml.

EXAMPLE 2

A 70 liter fermentor is charged with lactose (560 g), defatted soy bean powder (420 g), corn distillers' solubles (420 g), corn steep liquor (140 g), yeast extract (70 g), ammonium phosphate (70 g), sodium carbonate (35 g), soy bean oil (245 ml) and water (27 liters), and the mixture is sterilized at 120° C. for 5 minutes. Onto the medium is inoculated the culture broth (100 ml) obtained in Example 1 and then it is cultivated at 38° C. for 3 days with agitation and aeration of 35 liter/minute. The culture broth thus obtained has an activity of 13 ONPG unit/ml and 14 Lact unit/ml.

EXAMPLE 3

Figure 7:
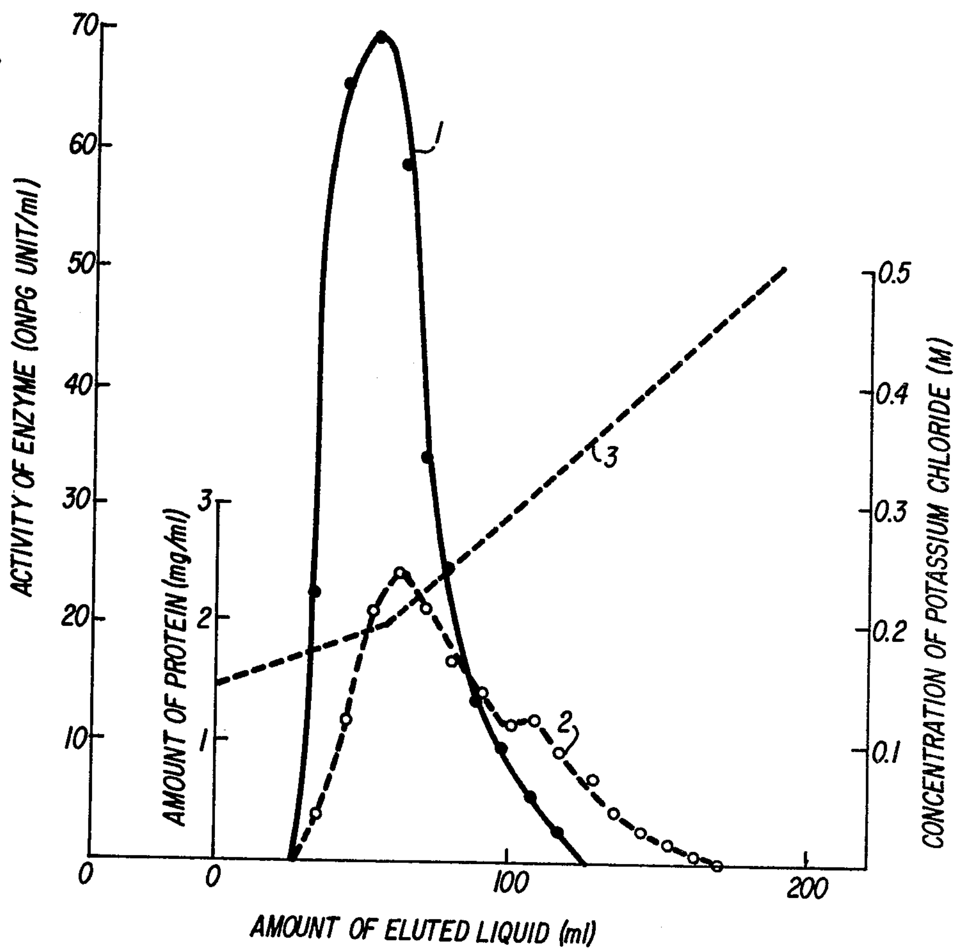

The culture broth obtained in Example 2 is filtered to remove the cells and is salted out with ammonium sulfate (53% saturation). The crude enzyme powder thus obtained has an activity of 1340 ONPG unit/g and 1460 Lact unit/g. A part of the crude enzyme is subjected to dialysis using a 0.01 M Tris-HCl buffer solution (pH 8.3) and adsorbed onto DEAE Sephadex A-25 and eluted with a 0.35 M aqueous potassium chloride solution. The eluted fraction having ONPG-hydrolyzing activity is further adsorbed onto DEAE Sephadex A-50 and then eluted to give the desired enzyme. The elution curve of the enzyme by a column chromatography on DEAE Sephadex A-50 is shown in the accompanying FIG. 7, wherein the enzyme is eluted with 0.15 to 0.4 M aqueous potassium chloride solution. In FIG. 7, the curve 1 is the activity of the enzyme, the curve 2 is the amount of protein, and the curve 3 is the concentration of potassium chloride. As is clear from FIG. 7, the peak of the activity is present at about 0.2 M of potassium chloride concentration. The enzyme has an activity of 33 ONPG unit/mg of protein and 41 Lact unit/mg of protein.

EXAMPLE 4

The crude enzyme powder used in Example 3 is dissolved in a 0.1 M acetate buffer to give an enzyme solution having an activity of 50 ONPG unit/ml or 10 ONPG unit/ml.

The enzyme solution (1 ml) is added to an 8% solution (9 ml) of whey powder in a 0.1 M acetate buffer (pH 6.0), and the mixture is reacted at a temperature of 40°, 50° or 60° C., and then, the amount of the produced glucose is measured, from which the rate of hydrolyzing lactose is calculated.

Figure 8:
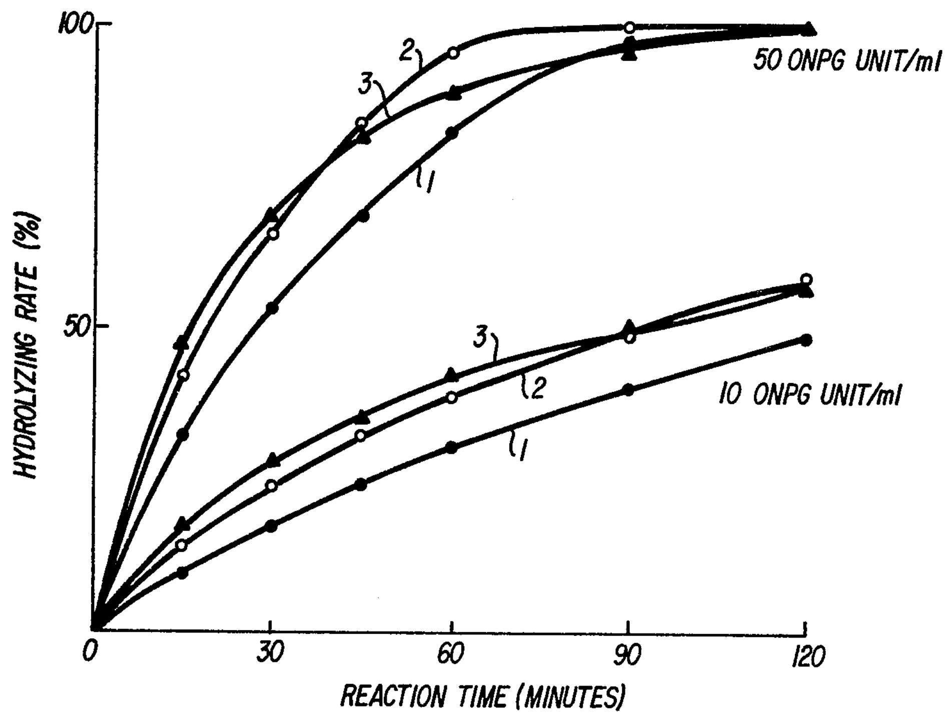

The relation between the hydrolyzing rate and the reaction time is shown in the accompanying FIG. 8, wherein the curves 1, 2 and 3 show the reaction temperature of 40° C. 50° C. and 60° C., respectively. As is clear from FIG. 8, when it is reacted for 90 minutes, the hydrolyzing rate is about 50% in case of the enzyme having an activity of 10 ONPG unit/ml and about 100% in case of that of 50 ONPG unit/ml.

EXAMPLE 5

The same enzyme solution (1 ml) prepared in Example 4 is added to a 10% skim milk (9 ml) and fresh milk (9 ml). The mixture is reacted at 5° C., and then, the amount of the produced glucose is measured with the lapse of time, and therefrom the rate of hydrolyzing lactose is calculated.

Figure 10:
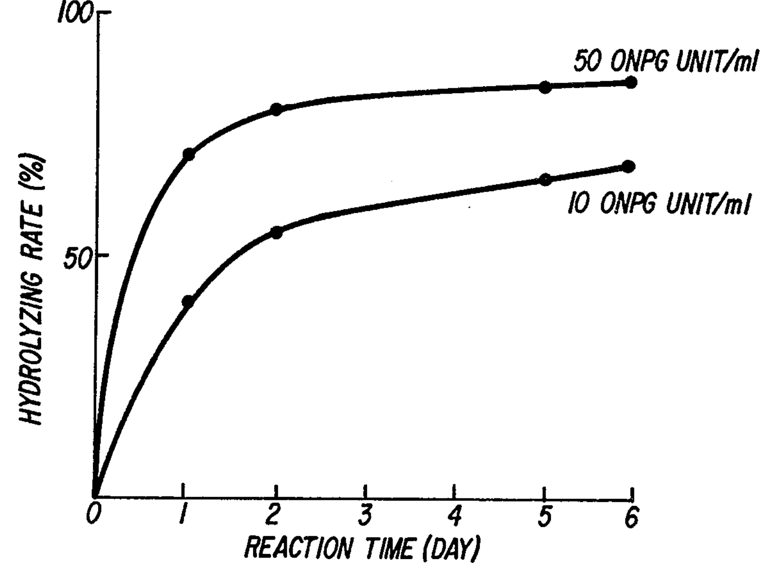
Figure 9:
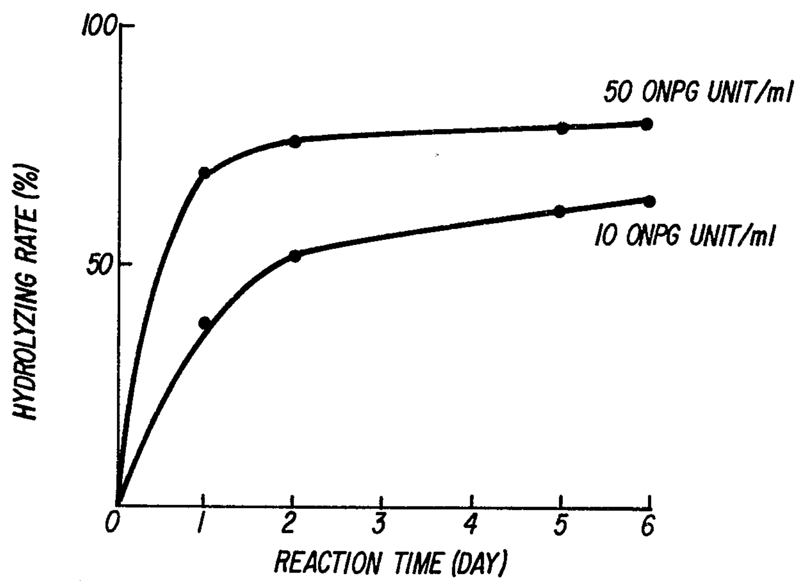

The relation between the hydrolyzing rate and the reaction time in case of skim milk and fresh milk is shown in FIG. 9 and FIG. 10, respectively. As is clear from these figures, in both milks, when the enzyme having an activity of 50 ONPG unit/ml is used, the hydrolyzing rate of about 50% is obtained by the reaction for 10 hours, and when the enzyme having 10 ONPG unit/ml is used, the hydrolyzing ratio of about 50% is obtained by the reaction for 2 days. Besides, in both cases, no coagulation of the reaction mixture is observed.

What is claimed is:

1. A lactase having a molecular weight of about $3\times10^5$, an optimum pH value of about 6.0, an optimum temperature of about 60° C. and at least 1 of the ratio of the activity for hydrolyzing lactose to the activity for hydrolyzing o-nitrophenyl-β-D-galactopyranoside.

2. A method for producing a lactase having a molecular weight of about $3\times10^5$, an optimum pH value of about 6, an optimum temperature of about 60° C., and a ratio of the activity for hydrolyzing lactose to the activity for hydrolyzing o-nitrophenyl-β-D-galactopyranoside of at least 1 to 1, said method comprising cultivating *Bacillus circulans* LOB 377 (ATCC 31382) and then isolating the enzyme from the culture broth.

3. A lactase produced by the cultivation of *Bacillus circulans* LOB 377 (ATCC 31382) having a molecular weight of about $3\times10^5$, an optimum pH value of about 6, an optimum temperature of about 60° C., and a ratio of the activity for hydrolyzing lactose to the activity for hydrolyzing O-nitrophenyl-β-D-galactopyranoside, of at least 1 to 1.

4. The method according to claim 2, wherein the cultivation is carried out at a temperature of 30° to 40° C. for a period of time of from 12 hours to 5 days.

* * * * *